United States Patent [19]

Umemura et al.

[11] Patent Number: 4,571,436

[45] Date of Patent: Feb. 18, 1986

[54] PROCESS FOR PRODUCING OPTICALLY ACTIVE CYCLOPENTENOLONES

[75] Inventors: Takeaki Umemura; Ayumu Inoue; Satoshi Mitsuda, all of Osaka, Japan

[73] Assignee: Sumitomo Chemical Company, Limited, Osaka, Japan

[21] Appl. No.: 612,122

[22] Filed: May 21, 1984

[30] Foreign Application Priority Data

May 25, 1983 [JP]  Japan ................................. 58-92943
Jun. 17, 1983 [JP]  Japan ................................ 58-109979

[51] Int. Cl.⁴ .............................................. C07C 45/65
[52] U.S. Cl. .................................... 568/354; 560/231; 260/456 R
[58] Field of Search ..................... 568/354; 260/456 R; 560/231

[56] References Cited

U.S. PATENT DOCUMENTS

| | | | |
|---|---|---|---|
| 3,009,944 | 11/1961 | Brunnberg | 260/467 |
| 3,189,654 | 6/1965 | Arthur | 568/351 |
| 4,000,179 | 12/1976 | Ayerst | 260/467 |
| 4,205,008 | 5/1980 | Martel et al. | 568/354 |
| 4,385,186 | 5/1983 | Matsuo et al. | 568/354 |

FOREIGN PATENT DOCUMENTS

| | | |
|---|---|---|
| 2558190 | 12/1975 | Fed. Rep. of Germany . |
| 2738647 | 3/1978 | Fed. Rep. of Germany . |
| 58-47495 | 3/1983 | Japan ................................... 560/231 |

OTHER PUBLICATIONS

Chem. Abst. vol. 85 (1976) p. 445, No. 61429y.
Patent Abstracts of Japan, vol. 2, No. 89, Jul. 21, 1978, p. 1439C78 and JP—A—5350397.

*Primary Examiner*—James H. Reamer
*Attorney, Agent, or Firm*—Cushman, Darby & Cushman

[57] ABSTRACT

Optically active cyclopentenolones, which are useful as an intermediate of pyrethroid insecticides, are produced from racemic cyclopentenolones according to the following procedures; (1) asymmetric hydrolysis of racemic carboxylate esters of the cyclopentenolones, (2) nitrate- or sulfonate-esterification of the asymmetrical hydrolysis products, and (3) hydrolysis of the esterification products.

23 Claims, No Drawings

PROCESS FOR PRODUCING OPTICALLY ACTIVE CYCLOPENTENOLONES

The present invention relates to a process for producing optically active cyclopentenolones represented by the formula (I),

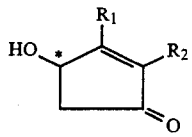

in which the mark * shows an asymmetric carbon; $R_1$ means a hydrogen atom or a $C_1$-$C_3$ alkyl group; and $R_2$ means a $C_1$-$C_6$ alkyl, $C_2$-$C_6$ alkenyl or $C_2$-$C_6$ alkynyl group.

The cyclopentenolones represented by the formula (I) above have been well known as the alcoholic moieties of a series of carboxylate esters, called synthetic pyrethroids, which have an excellent insecticial activity. The cyclopentenolone has an asymmetric carbon at the 4-position, so that it contains two optical isomers. It has been known that the insecticial activity of these pyrethroidal carboxylate esters having the (S)-cyclopentenolones as the alcoholic moiety are several times superior to those having the racemic or (R)-cyclopentenolones. For example, see Matsuo, et al, Pestic. Sci, 11, 202 (1980).

Therefore, there has been desired the development of an economical, convenient method for producing cyclopentenolones as represented by the formula (I).

Some methods have been known hitherto: for instance; U.S. Pat. No. 4,385,186 describes a method of the chemical optical resolution in which the racemic cyclopentenolone is converted to the corresponding acid phthalate, and then resolved with an optically active amine; and Japanese Unexamined Patent Publication Nos. Sho 58(1983)-31994 and Sho 58(1983)-47495 describes a method of the biochemical optical resolution in which the racemic cyclopentenolone is converted to an organic carboxylic acid ester thereof, and then the asymmetric hydrolysis is effected using an esterase. These processes, however, are not satisfactory as mentioned below.

Namely, although these methods yield the aimed (S)-isomer of cyclopentenolone, they yield at the same time an almost equal amount of the unwanted antipode thereof as the byproduct, in other words, the cyclopentenolone consisting of, or rich in, the (R)-isomer.

As mentioned before, the cyclopentenolone consisting of, or rich in, the (R)-isomer is inferior, with respect to the insecticidal activity, to the corresponding (S)-isomer, or (S)-isomer-rich cyclopentenolone.

In view of the fact that the unwanted byproduct is accumulated voluminously in the optical resolution process, a new process for utilizing the unwanted waste (R)-cyclopentenolone is being highly desired, in order that it is carried out in a commercial scale and for the purpose of rendering the optical resolution process commercially more feasible.

Besides, in these conventional processes, a sophisticated technique for isolation of each optical isomer is necessary in order to obtain it in a high purity. Such an isolation step is sometimes complicated, and therefore it is economically and technically restricted in commercial production.

In these conventional processes, the biochemical process using an esterase is excellent from the viewpoint of optical purity. However, even this process needs a precise separation step since it gives a mixture of an optically active cyclopentenolones with a high optical purity and an optically active cyclopentenolone carboxylate ester having the absolute configuration opposite to that of the cyclopentenolones. In order to separate the resulting optically active cyclopentenolone from the optically active cyclopentenolone carboxylate ester having the absolute configuration opposite to the cyclopentenolone, the mixture has to be further treated, for example, by silica gel chromatography.

Under these circumstances, the present inventors have investigated various processes for the production of optically active cyclopentenolones represented by the formula (I) from the mixture obtained by the biochemical optical resolution using an esterase. It has now found the optically active cyclopentenolones represented by the formula (I) mentioned above can be obtained by hydrolyzing a mixture of the optically active ester which is defined hereinbelow and is referred to as "ester-A" hereinafter, and the optically active carboxylate ester which is defined hereinbelow and is referred to as "ester-B", said mixture being prepared easily by esterifying a mixture obtained after the biochemical optical resolution of the carboxylic esters of racemic cyclopentenolone with an esterase.

The "ester-A" has the absolute configuration opposite to that of the compound of the formula (I) and is represented by the formula (III),

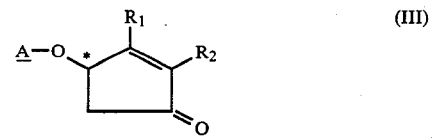

in which the mark *, $R_1$ and $R_2$ have the same meaning as above, and A means a nitro or —$SO_2X$ group, (X means a phenyl group which may have a methyl group, or a fluorine, chlorine, or bromine atom, at the para-position, or a $C_1$-$C_3$ alkyl group which may be substituted with one or more halogen atoms).

The "ester-B" has the absolute configuration opposite to that of the "ester-A" and is represented by the formula (II),

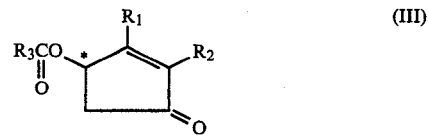

in which the mark *, $R_1$ and $R_2$ have the same meaning as above, and $R_3$ means a $C_1$-$C_3$ alkyl group.

In the present hydrolysis, the "ester-A" is converted into the desired optically active cyclopentenolone with inversion of configuration at the asymmetric carbon, while the "ester-B" is converted into the desired optically active cyclopentenolone retaining the configuration as it is, thereby only cyclopentenolones having the desired absolute configuration are effectively obtained. The inventors have accomplished the present invention on the basis of the findings that the present process is exceedingly advantageous for producing optically active cyclopentenolones of the formula (I), in conjunction with the process of biochemical optical resolution using an esterase.

Thus, an object of the present invention is to provide a process for producing optically active cyclopentenolones represented by the formula (I), by hydrolyzing a mixture of the optically active "ester-A" having the absolute configuration opposite to that of the objective cyclopentenolones and the optically active "ester-B" having the absolute configuration opposite to that of the "ester-A". The other objects will be obvious from the description which follows.

The mixture of an optically active "ester-A" and the optically active "ester-B" having the absolute configuration opposite to that of the "ester-A", which is the starting material of the present process is easily obtained by the following steps.

First step; an acylation of a racemic cyclopentenolone represented by the formula (VI),

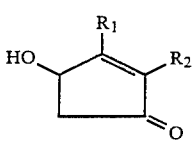

(VI)

in which $R_1$ and $R_2$ have the same meaning as above to produce an carboxylate ester of the formula (V),

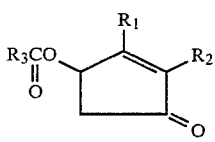

(V)

in which $R_1$, $R_2$ and $R_3$ have the same meaning as above.

Second step; an asymmetric hydrolysis of the carboxylate ester by an esterase originated from microorganisms or animal pancreas to produce a mixture of the optically active cyclopentenolones represented by the formula (IV),

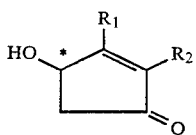

(IV)

in which the mark *, $R_1$ and $R_2$ have the same meaning as above and the optically active "ester-B" having the absolute configuration opposite to that of (IV).

Third step; an esterification of the asymmetric hydrolysis product mentioned above to produce the mixture of an optically active "ester-A" and the optically active "ester-B" having the absolute configuration opposite to that of the "ester-A".

According to the present invention, the mixture of (a) the optically active cyclopentenolones and (b) the optically active "ester-B" having the absolute configuration opposite thereto, said mixture having been obtained by the asymmetric hydrolysis using an esterase, can be converted to an objective optically active cyclopentenolones without any separation or isolation of (a) above from (b) above. In other words, cyclopentenolones of the formula (VI) can be converted entirely into the desired optically active cyclopentenolones of the formula (I).

The present process, for example, is illustrated schematically, as follows:

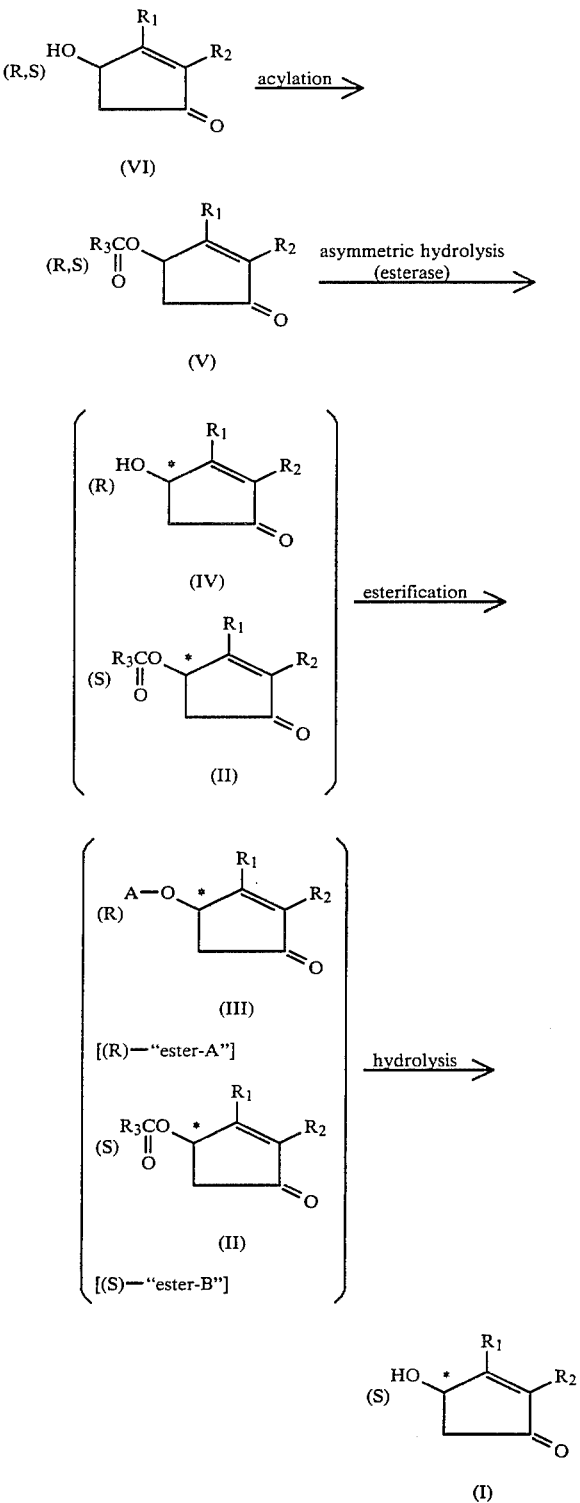

in which the mark *, $R_1$, $R_2$, $R_3$, and A have the same meaning as above.

As obvious from the above, there is no necessity to separate or isolate the cyclopentenolones of the formula (IV) composed of or rich in the (R)-isomer byproduct which is formed in the biochemical optical resolution using an esterase, but they can be converted into the objective, useful cyclopentenolones of the formula (I) composed of or rich in the (S)-isomer, according to the process of the invention. The present invention ensures the extremely advantageous production, even in a commercial scale, of the (S)-cyclopentenolones of the formula (I), in conjunction with the biochemical optical resolution technique of the cyclopentenolones of the formula (VI) using an esterase.

The more detailed illustration of the process of the invention will be given hereinafter.

In the present process, the hydrolysis of the mixture of the optically active "ester-A" and the optically active "ester-B" having absolute configuration opposite to that of the "ester-A" is carried out at a temperature within the range of 40° to 100° C., preferably from 70° to 100° C. from the standpoint of the period of time for the reaction.

This hydrolysis is carried out in water, but some organic solvent miscible to water may be added to, if necessary.

Examples of such solvents are alicyclic ethers including tetrahydrofuran, dioxane, etc.; lower aliphatic ketones such as acetone, methyl ethyl ketone, etc.; and non-protonic polar solvents such as dimethylformamide, dimethylsulfoxide, etc.

The hydrolysis is preferably carried out under an acidic condition. But the use of an acid is not always necessary since an acid of the formula (VII),

A—OH  (VII)

in which A has the same meaning as above serves to keep the hydrolysis condition under acidic, said acid being formed through the hydrolysis of the "ester-A" in the mixture. The hydrolysis of the "ester-B" in the mixture also proceeds efficiently without any additional acid. If desired, a suitable buffer solution may be employed in order to keep the hydrolysis condition under acidic.

The hydrolysis may be conducted in the presence of an alkali earth metal carbonate in order to neutralize a part of the acid of the formula (VII). An amount of the carbonate is not more than one equivalent to that of the "ester-A" contained in the mixture. The carbonate is, for example, calcium carbonate and barium carbonate.

The reaction mixture after the hydrolysis is subjected to a recovery procedure of the objective optically active cyclopentenolones, such as extraction with an organic solvent. If desired, the reaction mixture is concentrated before the extraction.

The starting mixture to be hydrolyzed, i.e., the mixture of the optically active "ester-A" and the optically active "ester-B" having the absolute configuration opposite thereto, is prepared by subjecting a mixture defined below to a nitrate- or sulfonate-esterification reaction, said mixture being composed of optically active cyclopentenolones of the formula (IV) and the optically active "ester-B" having the absolute configuration opposite thereto.

The nitrate-esterification reaction is carried out in the presence of a nitrating agent, such as a mixture of nitric acids such as nitric acid and fuming nitric acid with acetic anhydride, in which acetyl nitrate formed in situ substantially serves the nitrating agent. Alternatively, nitronium trifluoromethanesulfonate or N-nitrocollidinium tetrafluoroborate may be used. An amount of the nitrating agent is not critical, but generally not less than the equimolar amount to one mole of the cyclopentenolones in the mixture.

Although a solvent is not always necessary for the nitrate-esterification reaction, an inert organic solvent may be used, if desired. Examples of such solvents are halogenated hydrocarbons such as dichloromethane, dichloroethane, chloroform, carbon tetrachloride, etc.; nitroalkanes such as nitromethane, nitroethane, etc.; lower aliphatic carboxylic acids such as acetic acid, propionic acid, etc.; lower aliphatic carboxylate esters such as ethyl acetate; nitriles such as acetonitrile, etc.; aliphatic ketones such as acetone, methyl isobutyl ketone, etc.; and the like.

The temperature for the nitrate-esterification reaction may be, in general, from −40° to +30° C., preferably, −30° to +5° C.

The sulfonate-esterification reaction is effected with a sulfonic acid derivative represented by the formula (VIII),

X—SO$_2$—Y  (VIII)

in which Y means a halogen atom or a group represented by the formula, X—SO$_3$—, and X has the same meaning as above. Among the said sulfonic acid derivative, sulfonyl halides represented by the formula: X—SO$_2$—Y' in which Y' means a halogen atom and X has the same meaning as above, such as methanesulfonyl halide, p-toluenesulfonyl halide, etc., preferably methanesulfonyl chloride and p-toluenesulfonyl chloride are preferable from the easier availability.

An amount of the sulfonic acid derivative is not critical but it should be not less than one mole, usually, 1 to 1.2 moles to one mole of the optically active cyclopentenolone to be esterified.

The sulfonate-esterification reaction is preferably carried out in the presence of a base such as trialkylamine, particularly triethylamine. An amount of the base employed may, in general, be 1 to 1.5 moles per mole of the sulfonic acid derivative employed.

The sulfonate-esterification reaction is usually carried out in an inert organic solvent, such as lower aliphatic ketones including acetone, methyl ethyl ketone, methyl isobutyl ketone, etc.; aromatic hydrocarbons including benzene, toluene, xylene, etc.; ethers including diethyl ether, diisopropyl ether, tetrahydrofuran, etc.; halogenated hydrocarbons including dichloromethane, dichloroethane, carbon tetrachloride, etc.; any mixtures of these solvents; and the like.

The sulfonate-esterification reaction is usually carried out at a temperature ranging from −40° to +30° C.

With respect to asymmetric hydrolysis of ester with esterase, any esterase including lipase can be used for treating the cyclopentenolone carboxylate ester represented by the formula (V) as long as the esterase can asymmetrically hydrolyze the ester. The asymmetric hydrolysis produces (a) the optically active cyclopentenolones having the formula (IV) and (b) the "ester-B" having absolute configuration opposite to that of (a).

In this asymmetric hydrolysis, the esterase originated from microorganisms or animal pancreas can be employed.

Examples of the microorganisms, which are not limitative, are strains belonging to Enterobacter, Arthrobacter, Brevibacterium, Pseudomonas, Alcaligenes, Flavobacterium, Micrococcus, Chromobacterium, Mycobacterium, Corynebacterium, Bacillus, Lactobacillus, Trichoderma, Candida, Saccharomyces, Rhodotorula, Cryptococcus, Torulopsis, Pichia, Penicillium, Aspergillus, Phizopus, Mucor, Aureobasidium, Actinomucor, Nocardia, Streptomyces, Acromobacter, and the like.

The typical strains belonging to these genuses are

| | | |
|---|---|---|
| (1) | *Enterobacter cloacae* | IFO 3320 |
| (2) | *Arthrobacter simplex* | IFO 3530 |
| (3) | *Brevibacterium ammoniagenes* | IFO 12072 |
| (4) | *Pseudomonas fluorescens* | IFO 3081 |
| (5) | *Alcaligenes faecalis* | IFO 12669 |
| (6) | *Flavobacterium arborescens* | IFO 3750 |
| (7) | *Micrococcus luteus* | OUT 8276 |
| (8) | *Chromobacterium viscosum* | ATCC 6918 |
| (9) | *Mycobacterium phlei* | IFO 3158 |
| (10) | *Corynebacterium equi* | ATCC 7699 |
| (11) | *Bacillus subtilis* | IFO 3026 |
| (12) | *Lactobacillus casei* | IFO 3322 |
| (13) | *Trichoderma viride* | IFO 4847 |
| (14) | *Saccharomyces rouxii* | IFO 0505 |
| (15) | *Candida utilis* | IFO 0396 |
| (16) | *Rhodotorula minuta* | IFO 0387 |
| (17) | *Cryptococcus albidus* | IFO 0378 |
| (18) | *Torulopsis candida* | IFO 0768 |
| (19) | *Pichia polimorpha* | IFO 1166 |
| (20) | *Penicillium frequentans* | IFO 5692 |
| (21) | *Aspergillus var asper* | IFO 5324 |
| (22) | *Rhizopus chinensis* | IFO 4737 |
| (23) | *Aureobasidium pullulans* | IFO 4464 |
| (24) | *Actinomucor elegans* | IFO 4022 |
| (25) | *Nocardia asteroides* | IFO 3424 |
| (26) | *Streptomyces griseus* | IFO 3356 |
| (27) | *Mucor javanicus* | IFO 4572 |
| (28) | *Achromobacter parvulus* | IFO 13181 |

These strains have been deposited at such depositories as American Type Culture Collection (ATCC); Osaka University, Faculty of Engineering, Osaka, Japan (OUT); or Institute of Fermentation, Osaka, Japan (IFO) and are available therefrom.

Such a microorganism is usually cultured in a liquid medium according to the conventional procedure. For example, a malt extract-yeast extract medium, prepared by dissolving 5.0 g of peptone, 10.0 g of glucose, 3.0 g of malt extract, and 3.0 g yeast extract, in one liter of water, and adjusting the pH to 6.5, is suitable for fungi and yeasts. A sugared bouillon medium, prepared by dissolving 10.0 g of glucose, 5.0 g of peptone, 5.0 g of meat extract, and 3.0 g of NaCl, in one liter of water, and adjusting the pH to 7.2, is suitable for bacteria. Such a liquid medium is sterilized, inoculated with a microorganism, and cultured, for example, in a reciprocating shaker, originarily for 1 to 3 days at 20° to 40° C. Alternatively, the culture may be effected on a solid medium, if desired.

Among those microorganisms illustrated above, the strains belonging to genuses Enterobacter, Arthrobacter, Brevibacterium, Pseudomonas, Alcaligenes, Chromobacterium, Mycobacterium, Bacillus, Trichoderma, Candida, Rhodotorula, Torulopsis, Aspergillus, Rhizopus, Mocor, Nocardia, Achromobacter, and Streptomyces, are preferable from the viewpoints of the esterase activity and the asymmetric yield.

Some of the esterase originated from the microorganisms above have been sold and easily available in the market. Examples of the commercially available esterase are lipase from Pseudomonas (manufactured by Amano Seiyaku), lipase from Aspergillus (Lipase AP, manufactured by Amano Seiyaku), lipase from Mucor (Lipase M-AP, manufactured by Amano Seiyaku), lipase from *Candida cylindracea* (Lipase MY, manufactured by Meito Sangyo), lipase from Alcaligenes (Lipase PL, manufactured by Meito Sangyo), lipase from Achromobacter (Lipase Al, manufactured by Meito Sangyo), lipase from Arthrobacter (Lipase Godo BSL, manufactured by Godo Shusei), lipase from Chromobacterium (manufactured by Toyo Jozo), lipase from *Rhizopus delemar* (Talipase, manufactured by Tanabe Seiyaku), lipase from Rhizopus (Lipase, Saiken, manufactured by Osaka Saikin Kenkyusho), etc.

As for the esterase originated from animal pancreas, steapsin and pancreatin may be employed.

The asymmetric hydrolysis is carried out by stirring or shaking a mixture of the carboxylate ester represented by the formula (V) and an esterase-containing liquor, such as cultured liquor of such microorganism, its filtrate, esterase extracted liquor and its concentrate, suspension of microorganism cells or aqueous solution containing crude or purified esterase preparation or animal pancreas esterase preparation. Also, immobilized cells or immobilized esterase may be employed.

The suitable temperature range for the asymmetric hydrolysis is from 10° to 70° C., preferably 50° to 65° C. in case of heat-resistant esterase originated from thermophilic microorganisms, and 20° to 50° C. in case of esterase having low heat-resistance.

The reaction period of time is ordinarily 3 to 48 hours. The period may be shortened when the reaction temperature is made higher or an amount of the enzyme used is made larger.

The pH of the mixture during the course of the reaction may preferably be 8–11 in case of the culture liquid of alkalo-philic microorganisms or alkaline esterase, and 5–8 in case of the culture liquid of not alkalo-philic microorganisms or esterase not durable to alkali. The use of a buffer solution is preferable, in order to neutralize the organic carboxylic acid formed in the hydrolysis and to keep the pH during the course of the reaction at the constant level. A buffer solution consisting of an inorganic acid salt such as sodium and potassium phosphates, etc., or of an organic acid salt such as sodium acetate, sodium citrate, etc. is suitable.

The carboxylate ester represented by the formula (V), as the substrate, may be used in a concentration of 1 to 50% by weight, preferably, 5 to 25% by weight on the basis of the reaction mass.

While, the carboxylate ester represented by the formula (V) can easily be prepared by any of the conventional processes, for example, by reacting a cyclopentenolone of the formula (VI) with an organic carboxylic acid anhydride, or with an organic carboxylic acid chloride in the presence of an organic base.

The process of the invention will be further illustrated in the following examples, which, however, should not be construed to be limitative.

In the following examples, chemical purity was analyzed by a gas chromatography, and optical isomer ratio of (R)- and (S)-isomers was analyzed by converting the isomers into their N-3,5-dinitrophenylcarbamate derivatives and then subjecting the derivatives to a high-performance liquid chromatography using an optically active stationary phase.

EXAMPLE 1

(i) Asymmetric hydrolysis step:

A buffer solution having pH 6.5 was prepared by adding an aqueous 3 N sodium hydroxide solution to 250 g of an aqueous 0.2 M potassium dihydrogenphosphate solution. To this buffer solution were added 3.0 g of an esterase originated from an Arthrobacter strain (Lipase Godo BSL) and, then, 98.6 g of racemic 2-methyl-3-(2-propynyl)-4-oxo-2-cyclopenten-1-yl acetate. The mixture was vigorously agitated at 40° C. for 17 hours, during the reaction the pH was controlled to keep at 6.5±0.2 with an aqueous 3 N sodium hydroxide solution. The reaction mixture was extracted with ethyl acetate, and the ethyl acetate layer was dried over anhydrous magnesium sulfate and then concentrated to give 79.37 g of a mixture of (R)-4-hydroxy-3-methyl-2-(2-propynyl)-2-cyclopenten-1-one and (S)-2-methyl-3-(2-propynyl)-4-oxo-2-cyclopenten-1-yl acetate with the contents of 46.4% and 51.1%, respectively.

Whilst, a portion of the mixture mentioned above was subjected to a silica gel column chromatography for the separation of the components. There were obtained (R)-4-hydroxy-3-methyl-2-(2-propynyl)-2-cyclopenten-1-one, with $[\alpha]_D^{23} -19.5°$ (c=1.42 in chloroform) and (R)-isomer/(S)-isomer ratio of 94.8/5.2, and (S)-2-methyl-3-(2-propynyl)-4-oxo-2-cyclopenten-1-yl acetate, with $[\alpha]_D^{23} +39.4°$ (c=1.25, in chloroform) and (R)-isomer/(S)-isomer ratio of 1.0/99.0.

(ii) Nitrate-esterification step:

Into a mixed solution of 3 g of fuming nitric acid and 9 g of acetic anhydride at a temperature of −5° to 10° C. was added dropwise 3.45 g of the mixture obtained in the step (i). After stirring for 30 minutes at that temperature, the reaction mixture was poured into 100 ml of ice-water, and the mixture was extracted with toluene. The toluene layer was washed sequentially with an aqueous 5% sodium bicarbonate solution and water, dried over anhydrous magnesium sulfate, and, then, concentrated to give 3.78 g of a mixture of (R)-3-methyl-4-nitroxy-2-(2-propynyl)-2-cyclopenten-1-one and (S)-2-methyl-3-(2-propynyl)-4-oxo-2-cyclopenten-1-yl acetate.

(iii) Hydrolysis step:

Into 1.94 g of the mixture obtained in the step (ii) above were added 0.10 g of calcium carbonate and 30 ml of water, and the mixture was refluxed for 4.5 hours. The reaction mixture was cooled to room temperature and subjected to a celite-filtration to remove the insoluble substance. The filtrate was saturated with sodium chloride, and then extracted with methyl isobutyl ketone. The organic layer was separated, washed with an aqueous saturated sodium chloride solution, dried over anhydrous magnesium sulfate, and, then, concentrated to give 1.40 g of (S)-4-hydroxy-3-methyl-2-(2-propynyl)-2-cyclopenten-1-one, with a chemical purity of 94.6%, $[\alpha]_D^{25} +17.1°$ (c=1.41, in chloroform), and (R)-isomer/(S)-isomer ratio of 6.5/93.5.

Excepting the optical rotation, the product was identical with the starting racemic 4-hydroxy-3-methyl-2-(2-propynyl)-2-cyclopenten-1-one in the characteristics of IR and NMR spectra and the retention time on gas chromatogram.

EXAMPLE 2

To 1.94 g of the mixture obtained in the step (ii) in Example 1 was added 30 ml of water, and the mixture was refluxed for 2.5 hours. Thereafter, the similar procedure to the step (iii) in Example 1 gave 1.37 g of (S)-4-hydroxy-3-methyl-2-(2-propynyl)-2-cyclopenten-1-one, with a chemical purity of 91.3%, $[\alpha]_D^{25} +17.0°$ (c=1.25, in chloroform), and (R)-isomer/(S)-isomer ratio of 6.7/93.3.

Excepting the optical rotation, the product was identical with the starting racemic 4-hydroxy-3-methyl-2-(2-propynyl)-2-cycloropenten-1-one in its characteristics of IR and NMR spectra and the retention time on gas chromatogram.

EXAMPLE 3

(i) Asymmetric hydrolysis step:

A buffer solution having pH 6.5 was prepared by adding an aqueous 3 N sodium hydroxide solution to 125 g of an aqueous 0.2 M potassium dihydrogenphosphate solution. To this buffer solution were added 1.5 g of an esterase originated from an Arthrobacter strain (Lipase Godo BSL) and, then, 49.8 g of racemic 2-methyl-3-(2-propenyl)-4-oxo-2-cyclopenten-1-yl acetate. The mixture was vigorously agitated at 40° C. for 17 hours, during the reaction the pH was controlled to keep at 6.5±0.2 with an aqueous 3 N sodium hydroxide solution. The reaction mixture was extracted with ethyl acetate, and the ethyl acetate layer was dried over anhydrous magnesium sulfate and then concentrated to give 43.14 g of a mixture of (R)-4-hydroxy-3-methyl-2-(2-propenyl)-2-cyclopenten-1-one and (S)-2-methyl-3-(2-propenyl)-4-oxo-2-cyclopenten-1-yl acetate with the contents of 44.7% and 55.0%, respectively.

Whilst, a portion of the mixture mentioned above was subjected to a silica gel column chromatography for the separation of the components. There were obtained (R)-4-hydroxy-3-methyl-2-(2-propenyl)-2-cyclopenten-1-one, with $[\alpha]_D^{25} -14.9°$ (c=1.19, in chloroform) and (R)-isomer/(S)-isomer ratio of 99.2/0.8, and (S)-2-methyl-3-(2-propenyl)-4-oxo-2-cyclopenten-1-yl acetate, with $[\alpha]_D^{25} +29.8°$ (c=1.22, in chloroform) and (R)-isomer/(S)-isomer ratio of 0/100.

(ii) Nitrate-esterification step:

Into a mixed solution of 3.5 g of fuming nitric acid and 10 g of acetic anhydride at a temperature of −5° to 10° C. was added dropwise 5.0 g of the mixture obtained in the step (i) above. After stirring for 30 minutes at that temperature, the reaction mixture was poured into 100 ml of ice-water, and the mixture was extracted with toluene. The toluene layer was washed sequentially with an aqueous 5% sodium bicarbonate solution and water, dried over anhydrous magnesium sulfate, and, then, concentrated to give 5.87 g of a mixture of (R)-3-methyl-4-nitroxy-2-(2-propenyl)-2-cyclopenten-1-one and (S)-2-methyl-3-(2-propenyl)-4-oxo-2-cyclopenten-1-yl acetate.

(iii) Hydrolysis step:

Into 1.96 g of the mixture obtained in the step (ii) above were added 0.10 g of calcium carbonate and 30 ml of water, and the mixture was stirred at a temperature of 85° to 90° C. for 3 hours. The reaction mixture was cooled to room temperature and subjected to a celite-filtration to remove the insoluble substance. The filtrate was saturated with sodium chloride, and then extracted with methyl isobutyl ketone. The organic layer was separated, washed with an aqueous saturated sodium chloride solution, dried over anhydrous magnesium sulfate, and, then, concentrated to give 1.17 g of (S)-4-hydroxy-3-methyl-2-(2-propenyl)-2-cyclopenten-1-one, with a chemical purity of 92.1%, $[\alpha]_D^{25} +12.3°$ (c=1.03, in chloroform), and (R)-isomer/(S)-isomer ratio of 7.0/93.0.

Excepting the optical rotation, the product was identical with the starting racemic 4-hydroxy-3-methyl-2-(2-propenyl)-2-cyclopenten-1-one in the characteristics of IR and NMR spectra and the retention time on gas chromatogram.

EXAMPLE 4

(ii) Sulfonate-esterification step:

Into a solution of 1.5 g of the mixture obtained in the step (i) in Example 1, in 3 g of acetone, at a temperature of −15° to 0° C., was added 0.65 g of triethylamine. Into the mixture thus-obtained, at the same temperature, was added dropwise a solution of 0.62 g of methanesulfonyl chloride in 2 g of acetone, during 10 minutes. After stirring at the same temperature for 1.5 hours, the reaction mixture was poured into 30 ml of an aqueous 1% hydrochloric acid, and the mixture was extracted with methylene chloride. The methylene chloride layer was washed with water, dried over anhydrous magnesium sulfate, and concentrated to give 1.80 g of a mixture of (R)-2-methyl-3-(2-propynyl)-4-oxo-2-cyclopenten-1-yl methansulfonate and (S)-2-methyl-3-(2-propynyl)-4-oxo-2-cyclopenten-1-yl acetate.

(iii) Hydrolysis step:

Into 1.80 g of the mixture obtained in the step (ii) above were added 0.09 g of calcium carbonate and 10 ml of water, and the resulting mixture was refluxed for 1.5 hours. The reaction mixture was cooled to room temperature, and poured into an aqueous 5% sodium bicarbonate solution. The mixture was extracted with ethyl acetate, and the ethyl acetate layer was dried over anhydrous magnesium sulfate and concentrated to give 1.20 g of (S)-4-hydroxy-3-methyl-2-(2-propynyl)-2-cyclopenten-1-one, with a chemical purity of 96.4%, $[\alpha]_D^{23} +19.2°$ (c=1.14, in chloroform), and (R)-isomer/(S)-isomer ratio of 5.6/94.4.

Excepting the optical rotation, the product was identical with the starting racemic 4-hydroxy-3-methyl-2-(2-propynyl)-2-cyclopenten-1-one in the characteristics of IR and NMR spectra and the retention time on gas chromatogram.

EXAMPLE 5

(ii) Sulfonate-esterification step:

Into a solution of 1.5 g of the mixture obtained in the step (i) in Example 3, in 3 g of acetone, at a temperature of −15° to 0° C., was added 0.60 g of triethylamine. Into the mixture thus-obtained, at the same temperature, was added dropwise a solution of 0.58 g of methanesulfonyl chloride in 2 g of acetone, during 15 minutes. After stirring at the same temperature for 3 hours, the reaction mixture was poured into 30 ml of an aqueous 1% hydrochloric acid, and the mixture was extracted with methylene chloride. The methylene chloride layer was washed with water, dried over anhydrous magnesium sulfate, and concentrated to give 1.92 g of a mixture of (R)-2-methyl-3-(2-propenyl)-4-oxo-2-cyclopenten-1-yl methanesulfonate and (S)-2-methyl-3-(2-propenyl)-4-oxo-2-cyclopenten-1-yl acetate.

(iii) Hydrolysis step:

Into 1.92 g of the mixture obtained in the step (ii) above were added 0.09 g of calcium carbonate and 10 ml of water, and the resulting mixture was refluxed for 2 hours. The reaction mixture was cooled to room temperature, and extracted with ethyl acetate. The ethyl acetate layer was dried over anhydrous magnesium sulfate, and concentrated to give 1.27 g of (S)-4-hydroxy-3-methyl-2-(2-propenyl)-2-cyclopenten-1-one, with a chemical purity of 85.0%, $[\alpha]_D^{23} +5.66°$ (c=0.92, in chloroform), and (R)-isomer/(S)-isomer ratio of 10.1/89.9.

Excepting the optical rotation, the product was identical with the starting racemic 4-hydroxy-3-methyl-2-(2-propenyl)-2-cyclopenten-1-one in the characteristics of IR and NMR spectra and the retention time on gas chromatogram.

EXAMPLE 6

(ii) Nitrate-esterification step:

A solution of 15.0 g of the mixture obtained in the step (i) in Example 1, in 20 g of methyl isobutyl ketone, was added dropwise into a mixed solution of 5.0 g of fuming nitric acid and 12.37 g of acetic anhydride, at a temperature of −20° C. After stirring at the same temperature for 1.5 hours, the reaction mixture was poured into ice-water. The organic layer was separated and washed sequentially with an aqueous 5% sodium bicarbonate solution and water to obtain a methyl isobutyl ketone solution containing (R)-3-methyl-4-nitroxy-2-(2-propynyl)-2-cyclopenten-1-one and (S)-2-methyl-3-(2-propynyl)-4-oxo-2-cyclopenten-1-yl acetate.

(iii) Hydrolysis step:

A mixture of 200 g of water and 0.8 g of calcium carbonate was heated to a temperature of 85° to 90° C. To the mixture was added dropwise the methyl isobutyl ketone solution obtained in the step (ii) above, while the methyl isobutyl ketone was azeotropically distilled off. The reaction mixture was stirred at the same temperature for additional 4 hours. After cooling, the pH of the reaction mixture was adjusted to 6.0 by addition of an aqueous sodium hydroxide solution. The resulting mixture was saturated with sodium chloride, and then extracted with methyl isobutyl ketone. The combined organic layer was concentrated to give 11.36 g of (S)-4-hydroxy-3-methyl-2-(2-propynyl)-2-cyclopenten-1-one, with a chemical purity of 93.6%, $[\alpha]_D^{25} +16.8°$ (c=1.32, in chloroform), and (R)-isomer/(S)-isomer ratio of 7.3/92.7.

Excepting the optical rotation, the product was identical with the starting racemic 4-hydroxy-3-methyl-2-(2-propynyl)-2-cyclopenten-1-one in the characteristics of IR and NMR spectra and the retention time on gas chromatogram.

EXAMPLE 7

(ii) Sulfonate-esterification step:

To a solution of 25.0 g of the mixture obtained in the step (i) in Example 1, in 62 g of dichloroethane, at a temperature of 0° to 5° C., was added 9.48 g of methanesulfonyl chloride. Then, 8.17 g of triethylamine was added dropwise to the resulting mixture during 1 hour. The mixture was stirred for additional 2 hours at the same temperature, and washed twice with water to obtain a dichloroethane solution containing (R)-2-methyl-3-(2-propynyl)-4-oxo-2-cyclopenten-1-yl methanesulfonate and (S)-2-methyl-3-(2-propynyl)-4-oxo-2-cyclopenten-1-yl acetate.

(iii) Hydrolysis step:

A mixture of 170 g of water and 2 g of calcium carbonate was heated to a temperature of 85° to 90° C. To the mixture was added dropwise the dichloroethane solution obtained in the step (ii) above, while the dichloroethane was azeotropically distilled off. The reaction mixture was stirred at the same temperature for additional 4 hours. After cooling, the reaction mixture was washed with 20 g of carbon tetrachloride, and the aqueous layer was adjusted to pH 6.0 with an aqueous sodium hydroxide solution, saturated with sodium chloride, and extracted with dichloroethane. The combined organic layer was concentrated to give 19.90 g of (S)-4-hydroxy-3-methyl-2-(2-propynyl)-2-cyclopenten-1-one, with a chemical purity of 95.5%, $[\alpha]_D^{25} + 19.8°$ (c=1.23, in chloroform), and (R)-isomer/(S)-isomer ratio of 4.3/95.7.

Excepting the optical rotation, the product was identical with the starting racemic 4-hydroxy-3-methyl-2-(2-propynyl)-2-cyclopenten-1-one in the characteristics of IR and NMR spectra and the retention time on gas chromatogram.

We claim:

1. A process for producing optically active cyclopentenolones represented by the formula (I),

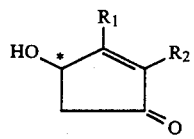
(I)

in which the mark * shows an asymmetric carbon; $R_1$ means a hydrogen atom or a $C_1$–$C_3$ alkyl group; and $R_2$ means a $C_1$–$C_6$ alkyl, $C_2$–$C_6$ alkenyl, or $C_2$–$C_6$ alkynyl group, which comprises hydrolyzing under acid conditions a mixture of an optically active ester having the absolute configuration opposite to that of the compound of the formula (I) and being represented by the formula (III),

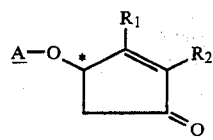
(III)

in which the mark *, $R_1$ and $R_2$ have the same meaning as above, and A means a nitro or —$SO_2X$ group, X means a phenyl group which may have a methyl group, or a fluorine, chlorine, or bromine atom, at the para-position, or a $C_1$–$C_3$ alkyl group which may be substituted with one or more halogen atoms, and an optically active ester having the absolute configuration opposite to that of the ester of the formula (III), and being represented by the formula (II),

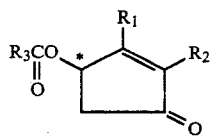
(III)

in which the mark *, $R_1$ and $R_2$ have the same meaning as above, and $R_3$ means a $C_1$–$C_3$ alkyl group.

2. A process according to claim 1, wherein the hydrolysis is carried out in the presence of an alkali earth metal carbonate in an amount of not more than one equivalent on the basis of that of the optically active ester of the formula (III).

3. A process for producing optically active cyclopentenolones represented by the formula (I),

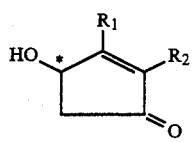
(I)

in which the mark * shows an asymmetric carbon; $R_1$ means a hydrogen atom or a $C_1$–$C_3$ alkyl group; and $R_2$ means a $C_1$–$C_6$ alkyl, $C_2$–$C_6$ alkenyl or $C_2$–$C_6$ alkynyl group, which comprises (1) subjecting to an esterification reaction a mixture of optically active cyclopentenolones having the absolute configuration opposite to that of the compound of the formula (I), and being represented by the formula (IV),

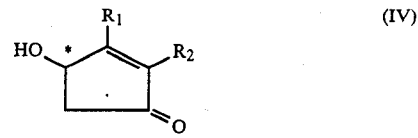
(IV)

in which the mark *, $R_1$ and $R_2$ have the same meaning as above, and optically active esters having the absolute configuration opposite to that of the compounds of the formula (IV), and being represented by the formula (II),

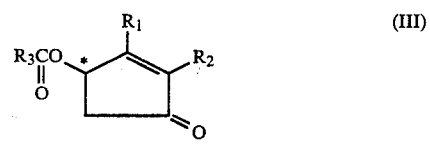
(III)

in which the mark *, $R_1$ and $R_2$ have the same meaning as above, and $R_3$ means a $C_1$–$C_3$ alkyl group, thereby the mixture is converted into a mixture of optically active esters having the absolute configuration same as that of the compound of the formula (IV), and being represented by the formula (III),

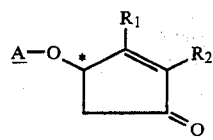
(III)

in which the mark *, $R_1$ and $R_2$ have the same meaning as above, and A means a nitro or —$SO_2X$ group, X means a phenyl group which may have a methyl group, or a fluorine, chlorine, or bromine atom, at the para-position, or a $C_1$–$C_3$ alkyl group which may be substituted with one or more halogen atoms, and the compounds of the formula (II); and (2) hydrolyzing the mixture obtained in (1).

4. A process according to claim 3, wherein the hydrolysis is carried out in the presence of an alkali earth metal carbonate in an amount of not more than one equivalent on the basis of that of the optically active ester of the formula (III).

5. A process according to claim 3, wherein the esterification reaction is a nitrate-esterification reaction using a nitrating agent.

6. A process according to claim 5, wherein the nitrating agent is a mixture of (a) nitric acid or fuming nitric acid and (b) acetic anhydride.

7. A process according to claim 3, wherein the esterification reaction is a sulfonate-esterification reaction using a sulfonic acid derivative represented by the formula,

X—$SO_2$—Y in which Y means a halogen atom or a group represented by the formula, X—SO$_3$—, and X has the same meaning as above.

8. A process according to claim 7, wherein the sulfonic acid derivative is a sulfonyl halide represented by the formula, X—SO$_2$—Y' in which Y' means a halogen atom and X has the same meaning as above.

9. A process according to claim 8, wherein the sulfonyl halide is methanesulfonyl chloride or p-toluenesulfonyl chloride.

10. A process according to claim 7, wherein the sulfonate-esterification reaction is carried out in the presence of a base.

11. A process according to claim 10, wherein the base is triethylamine.

12. A process for producing optically active cyclopentenolones represented by the formula (I),

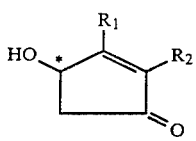
(I)

in which the mark * shows an asymmetric carbon; R$_1$ means a hydrogen atom or a C$_1$-C$_3$ alkyl group; R$_2$ means a C$_1$-C$_6$ alkyl, C$_2$-C$_6$ alkenyl, or C$_2$-C$_6$ alkynyl group, which comprises (1) asymmetrically hydrolyzing under acid conditions carboxylate esters represented by the formula (V),

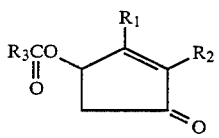
(V)

in which R$_1$ and R$_2$ have the same meaning as above, and R$_3$ means a C$_1$-C$_3$ alkyl group, with an esterase originated from microorganisms or animal pancreas to provide a mixture of optically active cyclopentenolones having the absolute configuration opposite to that of the compound of the formula (I), and being represented by the formula (IV),

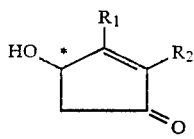
(IV)

in which the mark *, R$_1$ and R$_2$ have the same meaning as above, and optically active carboxylate esters having the absolute configuration opposite to that of the compound of the formula (IV) and being represented by the formula (II),

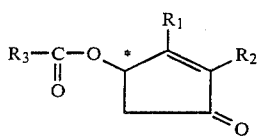
(II)

in which the mark *, R$_1$, R$_2$ and R$_3$ have the same meanings as above; (2) subjecting the mixture thus obtained to an esterification reaction to convert the mixture into a mixture of optically active esters having the absolute configuration same as that of the compound of the formula (IV) and being represented by the formula (III),

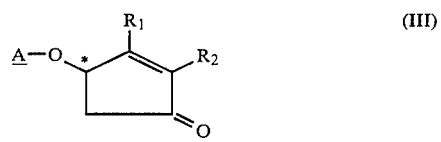
(III)

in which the mark *, R$_1$ and R$_2$ have the same meaning as above, and A means a nitro or —SO$_2$X group, X means a phenyl group which may have a methyl group, or a fluorine, chlorine, or bromine atom, at the para-position, or a C$_1$-C$_3$ alkyl group which may be substituted with one or more halogen atoms, and the compound of the formula (II); and (3) hydrolyzing under acid conditions the mixture thus obtained.

13. A process according to claim 12, wherein the hydrolysis is carried out in the presence of an alkali earth metal carbonate in an amount of not more than one equivalent on the basis of that of the optically active ester of the formula (III).

14. A process according to claim 12, wherein the esterification reaction is a nitrate-esterification reaction using a nitrate agent.

15. A process according to claim 14, wherein the nitrating agent is a mixture of (a) nitric acid or fuming nitric acid and (b) acetic anhydride.

16. A process according to claim 12, wherein the esterification reaction is a sulfonate-esterification reaction using a sulfonic acid derivative represented by the formula,

X—SO$_2$—Y in which Y means a halogen atom or a group represented by the formula, X—SO$_3$—, and X has the same meaning as above.

17. A process according to claim 16, wherein the sulfonic acid derivative is a sulfonyl halide represented by the formula, X—SO$_2$—Y' in which Y' means a halogen atom and X has the same meaning as above.

18. A process according to claim 17, wherein the sulfonyl halide is methanesulfonyl chloride or p-toluenesulfonyl chloride.

19. A process according to claim 16, wherein the sulfonate-esterification reaction is carried out in the presence of a base.

20. A process according to claim 19, wherein the base is triethylamine.

21. A process according to any of claims 1 through 23, wherein R$_1$ is a methyl group and R$_2$ is a 2-propenyl or 2-propynyl group.

22. A process according to claim 3 wherein R$_1$ is a methyl group and R$_2$ is a 2-propenyl or 2-propynyl group.

23. A process according to claim 12 wherein R$_1$ is a methyl group and R$_2$ is a 2-propenyl or 2-propynyl group.

* * * * *